United States Patent
Mooney et al.

(10) Patent No.: US 9,474,877 B2
(45) Date of Patent: Oct. 25, 2016

(54) TRANSURETHRAL CATHETER KIT, AND SYRINGE ASSEMBLY SUITABLE FOR USE IN CORRECTLY INFLATING A TRANSURETHRAL CATHETER

(71) Applicant: University of Limerick, Limerick (IE)

(72) Inventors: Rory Mooney, Ballinacurra (IE); Niall David, Mount Merrion (IE); Michael Walsh, Glin (IE); Eoghan Cunnane, Ardnacrusha (IE)

(73) Assignee: University of Limerick, Limerick (IE)

( * ) Notice: Subject to any disclaimer, the term of this patent is extended or adjusted under 35 U.S.C. 154(b) by 0 days.

(21) Appl. No.: 14/267,546

(22) Filed: May 1, 2014

(65) Prior Publication Data

US 2015/0112312 A1 Apr. 23, 2015

(30) Foreign Application Priority Data

Oct. 18, 2013 (EP) .................................. 13189442

(51) Int. Cl.
*A61M 25/00* (2006.01)
*A61M 25/10* (2013.01)
(Continued)

(52) U.S. Cl.
CPC ..... *A61M 25/0017* (2013.01); *A61M 25/1018* (2013.01); *A61M 25/10181* (2013.11); *A61M 25/10182* (2013.11); *A61M 25/10184* (2013.11); *A61M 25/10186* (2013.11); *A61M 2039/242* (2013.01); *A61M 2205/19* (2013.01); *F16K 17/048* (2013.01); *F16K 17/06* (2013.01)

(58) Field of Classification Search
CPC .................... A61M 25/0017; A61M 25/1018;
A61M 25/10181; A61M 25/10182; A61M 25/10184; A61M 25/10185; A61M 25/1025; A61M 2210/1078; A61M 2210/1085; A61M 2210/1089; A61M 2210/1092; A61M 2210/1096; A61M 25/10186; A61M 25/10187; A61M 5/48; A61M 5/482; A61M 5/484; A61M 5/486; A61M 5/488; A61M 16/209; A61M 2205/3351; A61M 2205/3355; A61M 2205/3337; A61B 2019/302; A61B 19/30; A61F 5/4405; F16K 17/00; F16K 17/02; F16K 17/04; F16K 17/0406; F16K 17/0413; F16K 17/06; F16K 17/20
USPC ............... 604/540, 544, 93.01, 95.03, 96.01, 604/97.01, 97.02, 97.03, 98.01, 99.01, 604/99.02, 99.03
See application file for complete search history.

(56) References Cited

U.S. PATENT DOCUMENTS 3,207,179 A * 9/1965 Klagues ........................ 137/879
3,796,228 A * 3/1974 Bedo ....................... F16K 17/04
137/536

(Continued)

FOREIGN PATENT DOCUMENTS

| WO | WO-94/02195 | 2/1994 |
| WO | WO-95/33510 | 12/1995 |
| WO | WO-2013/074763 | 5/2013 |

*Primary Examiner* — Adam Marcetich
(74) *Attorney, Agent, or Firm* — Cesari and McKenna LLP (57) ABSTRACT

A transurethral catheter kit containing a balloon catheter and a syringe assembly adapted for inflation of the balloon. The syringe assembly includes a syringe and a nozzle incorporating a narrow bore proximal to a pressure relief valve. The narrow bore serves to resist the flow of fluid between the syringe and the balloon, thereby avoiding a rapid pressure increase in the balloon that can result in damage to tissues or premature activation of the pressure relief valve. Also provided is a method for correctly placing a transurethral balloon catheter in a patient using the kit.

17 Claims, 10 Drawing Sheets

(51) Int. Cl.
   *F16K 17/04*   (2006.01)
   *F16K 17/06*   (2006.01)
   *A61M 39/24*   (2006.01)

(56) References Cited

U.S. PATENT DOCUMENTS

| | | | | |
|---|---|---|---|---|
| 3,983,879 | A * | 10/1976 | Todd | A61M 25/1036 |
| | | | | 604/915 |
| 3,985,141 | A * | 10/1976 | Stanley et al. | 128/207.15 |
| 4,000,741 | A * | 1/1977 | Binard et al. | 604/121 |
| 4,059,017 | A * | 11/1977 | Settlemyer et al. | 73/706 |
| 4,064,897 | A * | 12/1977 | Weber | 137/224 |
| 4,116,201 | A * | 9/1978 | Shah | 128/207.15 |
| 4,329,985 | A * | 5/1982 | Bonchek | 604/28 |
| 4,403,988 | A * | 9/1983 | Binard et al. | 604/118 |
| 4,439,185 | A | 3/1984 | Lundquist | |
| 4,552,558 | A | 11/1985 | Muto | |
| 4,623,335 | A * | 11/1986 | Jackson | 604/118 |
| 4,671,786 | A * | 6/1987 | Krug | 604/6.1 |
| 6,142,980 | A * | 11/2000 | Schalk | 604/247 |
| 6,520,977 | B2 * | 2/2003 | Piraka | A61M 25/10 |
| | | | | 606/193 |
| 2003/0106591 | A1 * | 6/2003 | Saurwein | F16K 17/06 |
| | | | | 137/540 |
| 2004/0138615 | A1 * | 7/2004 | Lombardi | 604/118 |
| 2004/0230169 | A1 * | 11/2004 | Felix et al. | 604/317 |
| 2006/0149189 | A1 * | 7/2006 | Diamond et al. | 604/118 |
| 2006/0161102 | A1 * | 7/2006 | Newcomb et al. | 604/96.01 |
| 2008/0147007 | A1 * | 6/2008 | Freyman | A61M 5/14526 |
| | | | | 604/151 |
| 2008/0200871 | A1 * | 8/2008 | Slater | A61M 25/0097 |
| | | | | 604/96.01 |
| 2010/0292640 | A1 * | 11/2010 | Kien | 604/99.02 |
| 2011/0082444 | A1 * | 4/2011 | Mayback et al. | 604/544 |
| 2011/0088696 | A1 * | 4/2011 | Ratner | 128/205.24 |
| 2013/0131626 | A1 * | 5/2013 | Thompson et al. | 604/500 |
| 2013/0165905 | A1 * | 6/2013 | Pinchuk et al. | 604/544 |

* cited by examiner

TRANSURETHRAL CATHETER KIT, AND SYRINGE ASSEMBLY SUITABLE FOR USE IN CORRECTLY INFLATING A TRANSURETHRAL CATHETER

CROSS REFERENCE TO RELATED APPLICATIONS

This application claims priority from European Patent Application No. 13189442.0, filed on Oct. 18, 2013, the contents of this application are hereby incorporated by reference in its entirety.

INTRODUCTION

The invention relates to a transurethral catheter (TUC) kit comprising a balloon catheter and a syringe adapted for inflation of the balloon. The invention also relates to a method for correctly placing a transurethral balloon catheter in a patient.

Approximately 10-25% of all hospitalized patients are catheterized during admission. Transurethral balloon catheters generally comprise a catheter having an inflation lumen and a drainage lumen, and an inflatable balloon disposed on a distal end of the catheter and in fluid communication with the inflation lumen. An opposite end of the inflation lumen is attached to a syringe for the purpose of inflating the balloon. The purpose of the balloon is to anchor the catheter in place once it has been correctly positioned with the distal end of the drainage lumen and the balloon disposed within the bladder. Thus, once inflated, the balloon acts as a stopper preventing unwanted removal or movement of the catheter. The problem of incorrect positioning of transurethral balloon catheters is well recognized in the field, with one study reporting that accidental inflation of the catheters balloon in the urethra accounting for 12% for all catheter-related complications. This occurs when a clinician incorrectly positions the catheter, and inflates the balloon while it is located within the confined space of the urethra, causing considerable pain to the patient and damage and in some cases rupture of the urethra. In addition to causing immediate trauma to the patient, this also results in long-term health problems for the patient. Globally, iatrogenic urethral trauma post TUC has an incidence of 1%; specifically, the rate of urinary track infections, cystitis, and septicaemia-bacteraemia occurring post-TUC are 12.72%, 3.45%, and 1.9%, respectively.

Attempts to address this problem in percutaneous transluminal angioplasty procedures have been suggested in the prior art. For example, WO95/33510 (Willis, Alan) discloses a transurethral catheter assembly that incorporates a pressure relief valve in the syringe assembly. The valve is configured to actuate, and thus exhaust inflation fluid from the syringe, when the pressure in the syringe reaches a defined threshold. Thus, if a user attempts to inflate the balloon in the urethra, the pressure build-up in the balloon causes the pressure relief valve to actuate, thereby preventing further inflation of the balloon and providing an indication to the user that the catheter has been incorrectly positioned.

STATEMENT OF INVENTION

Figure 2:
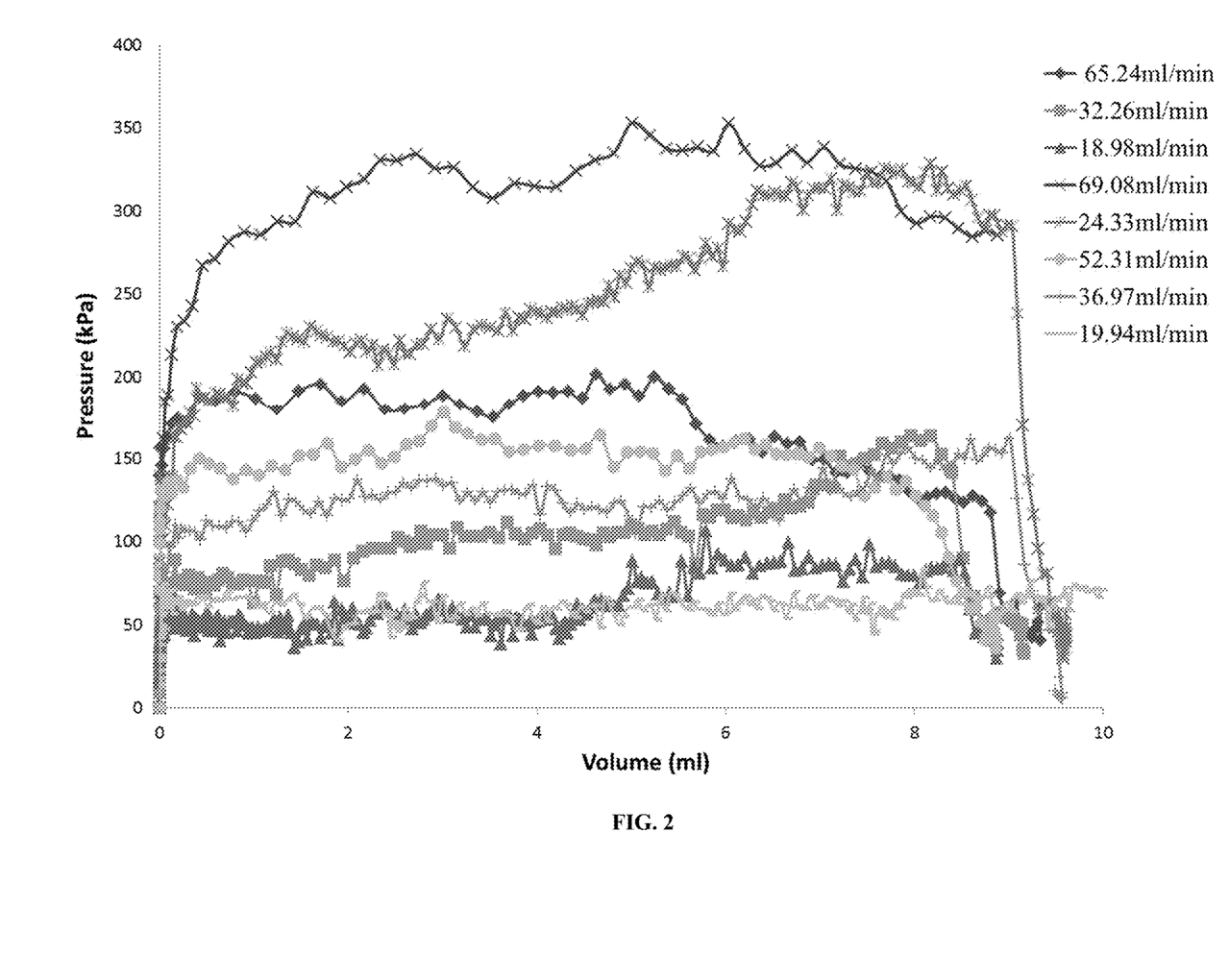
FIG. 2: Pressure vs. volume graph of 8 different users inflating a similar brand catheter which highlights user variability using a normal syringe.
Figure 3:
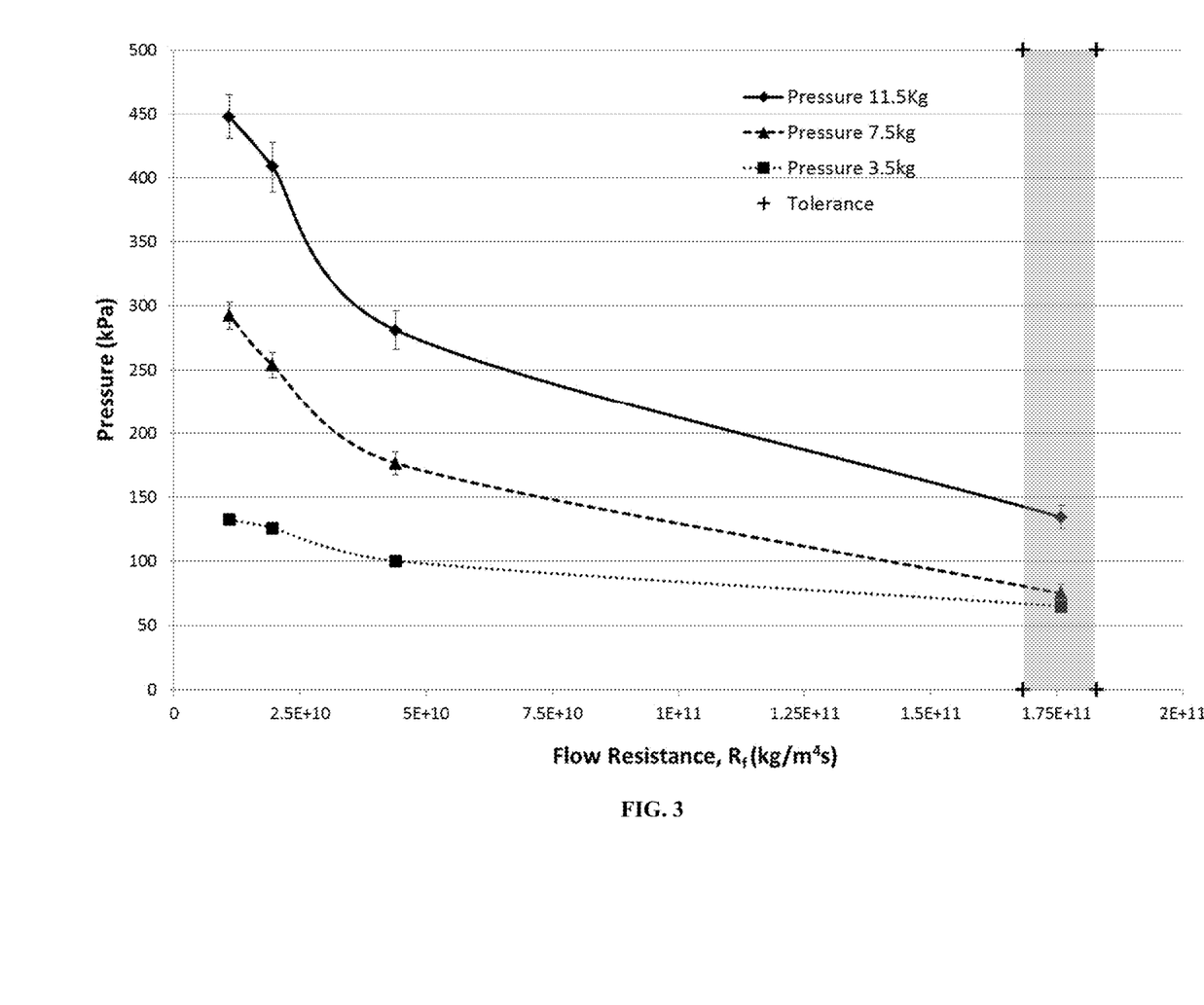
FIG. 3: Pressure vs. flow resistance for the three weights that correspond to high, normal and low forces, shaded area is tolerance of highest resistance that will be used in prototype.
Figure 4:
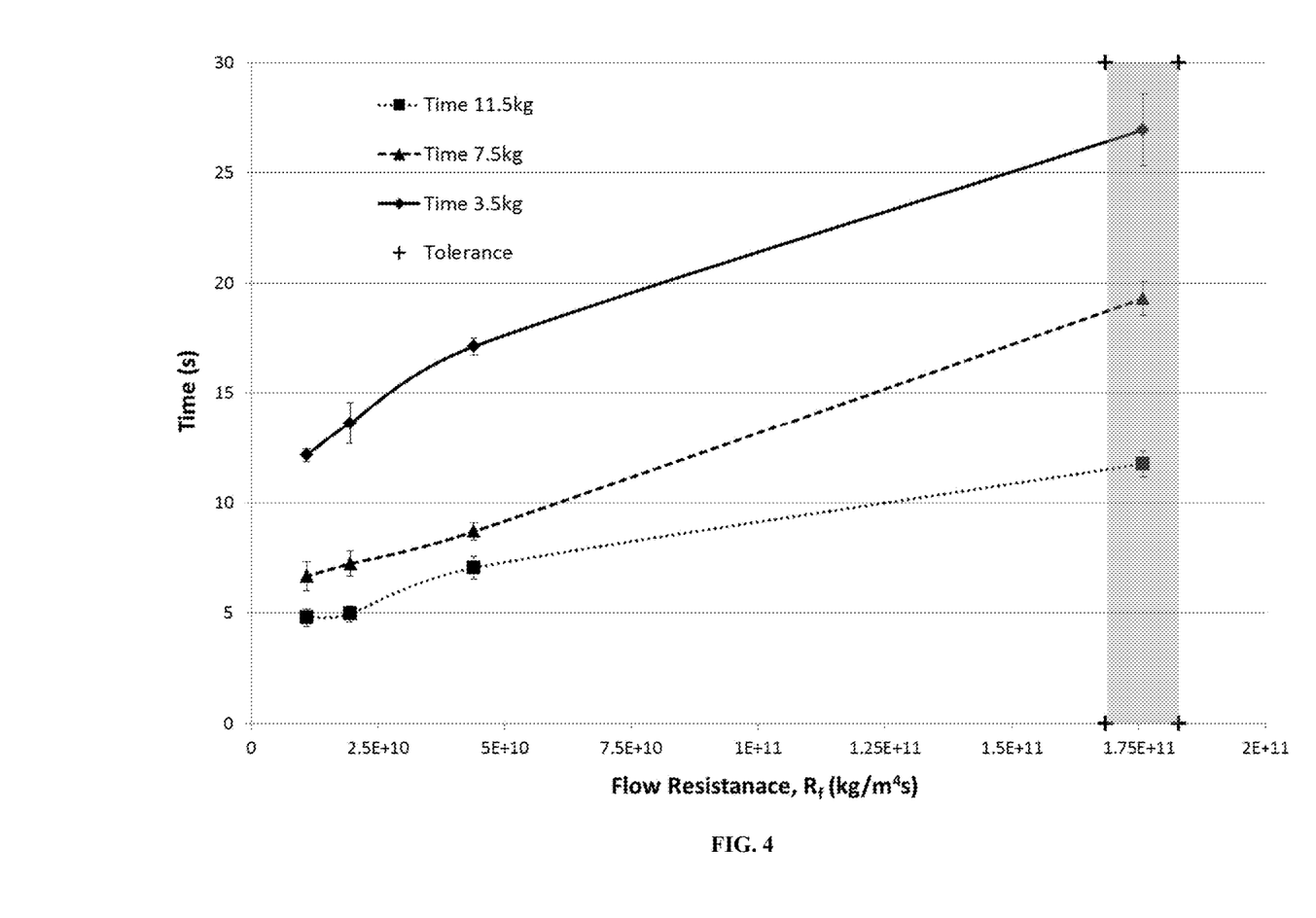
FIG. 4: Time vs. flow resistance for the three weights that correspond to high, normal and low forces, shaded area is tolerance of highest resistance that will be used in prototype.

The Applicant has surprisingly discovered that pressure relief valves employed with current transurethral balloon catheter kits are prone to premature actuation due to rapid increases in balloon pressure during the initial stages of plunger depression. This is shown in FIG. 2, and is caused by users exerting too much pressure on the syringe during the initial stages of plunger depression. Thus, in the case of most users, too much pressure is applied to the syringe initially, and the pressure increases rapidly at a stage where there is minimal inflation of the balloon, causing the pressure relief valve to actuate with consequent loss of pressure and failure to inflate the balloon. Further, if the catheter balloon is incorrectly positioned the urethral resistance pressure is superseded by the rapid plunger deployment preventing the safety valve from actuating in time to prevent urethral damage (see the initial slope of the graphs in FIG. 2). It can also be seen from FIG. 2 that a safety valve actuating pressure from these results would be set at 350kPa to allow for all users to be able to inflate the balloon when the catheter balloon is correctly positioned in the bladder. However, it can also be seen from FIG. 2 that some users can inflate the catheter balloon at pressures below 100 kPa. Consequently, these users would be able to inflate the balloon in the urethra despite the presence of a safety valve as the actuating pressure of the valve is significantly higher than the inflation pressure of the catheter balloon in the urethra for some users. The Applicant has addressed this problem by providing the syringe with resistance means configured to provide a sufficient resistance to flow of the inflation fluid such that the inflation pressure does not vary greatly across a range of users (here represented by a range of applied force F from 3.5 kgF to 11.5 kgF, which correlates with the levels of force applied by humans of different size and strength). Thus, when a resistance to flow, $R_f$, of 1.65E+11 to 1.85E+11 $kg/m^4 s$ is applied to the fluid in the syringe assembly, the inflation pressure across all applied forces was less than 150 kPa, and across the force range of 3.5-7.5kgF the inflation pressure was less than 100 kPa (FIG. 3). Moreover, at this $R_f$ value, the inflation times for the balloon were in the range of 12-27 seconds (FIG. 4). Therefore, providing the resistance to flow $R_f$ range of 1.65E+11 to 1.85E+11 $kg/m^4 s$ maintains the inflation pressure at a relatively low value across a range of users, while allowing inflation to be completed in a reasonable timeframe. Additionally, the resistance to flow values provided above keep the inflation pressure differential (i.e. the difference in inflation pressure across a range of users) within a tight range, 65 kPa-135 kPa, thereby ensuring that the inflation pressure does not vary greatly across a range of users, and can be more easily maintained at a level that is below the threshold pressure of the pressure release valve (which will generally be in the 100-150 kPa range) and prevent rapid rises in pressure which can cause damage to the urethra when the balloon is incorrectly positioned within the urethra. In one embodiment, the resistance to flow is provided by a narrow bore in the nozzle of the syringe, typically having a cross sectional area of 0.04mm² to 0.06mm². This results in more controlled depression of the plunger across a range of actuation pressures, avoiding a rapid pressure increase at the initial stages of inflation and consequent premature actuation of the pressure relief valve.

Figure 1A:
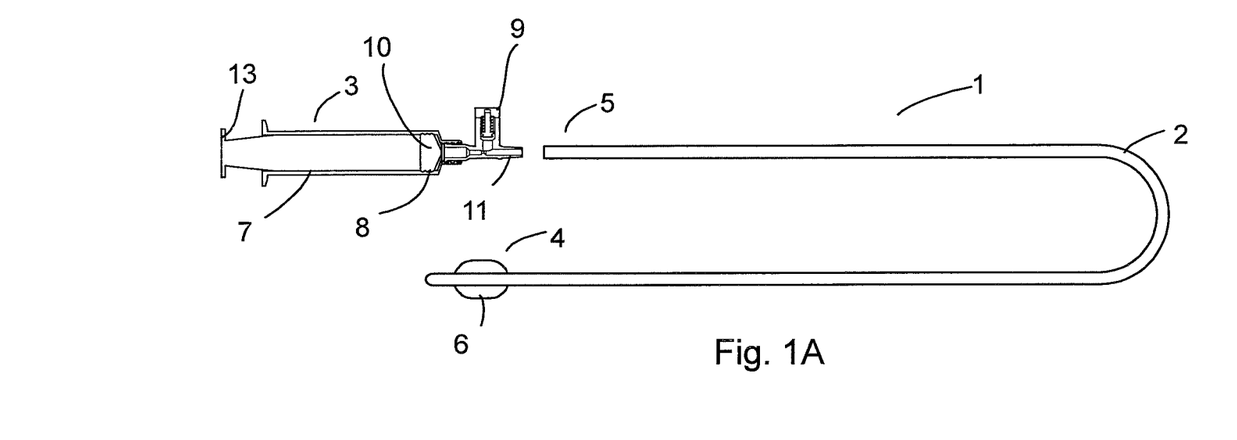
FIG. 1A is an illustration of a transurethral catheter kit of the invention, shown in an assembled mode.
Figure 1B:
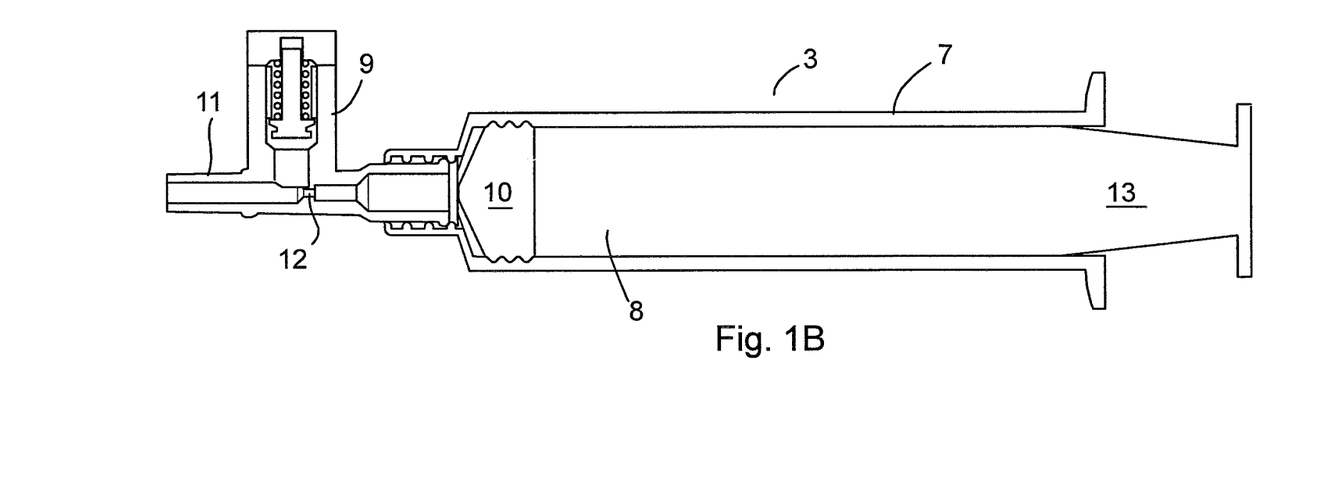
FIGS. 1B to 1C show a syringe assembly according to the invention and forming part of the transurethral catheter kit of the invention.
Figure 1C:
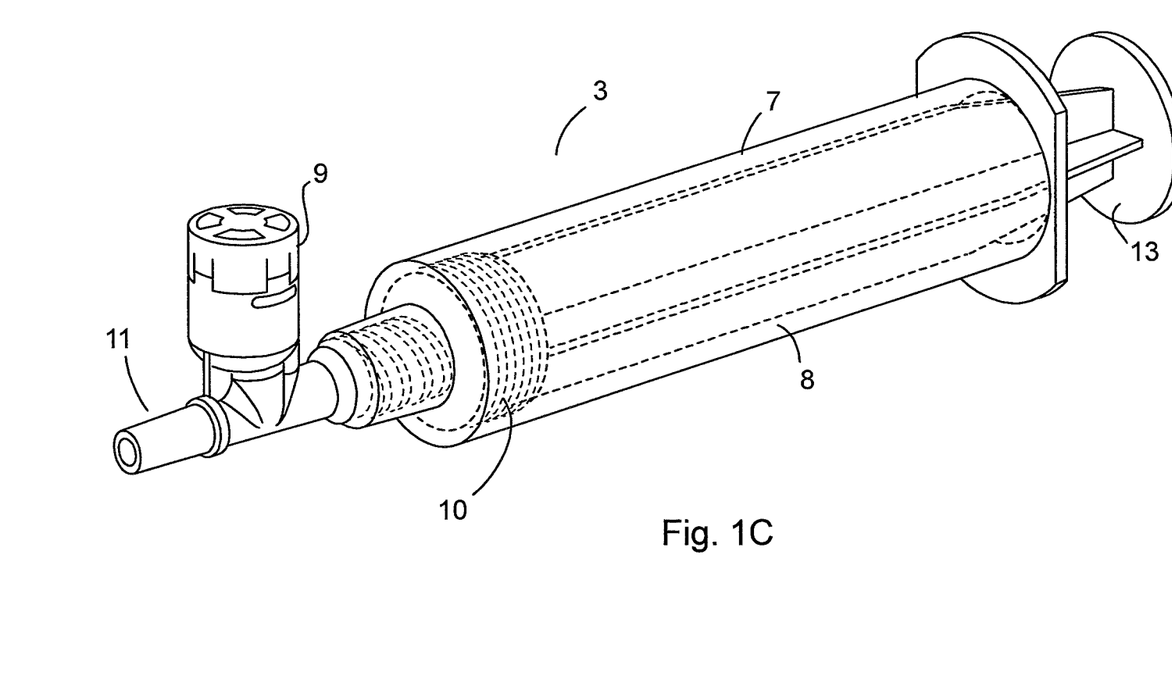

Accordingly, in a first aspect, the invention provides a transurethral catheter kit, typically a transurethral catheter kit, indicated generally by the reference numeral (1) and comprising a catheter (2) and a syringe assembly (3), the catheter having a distal end (4) and a proximal end (5), an inflatable balloon (6) disposed on the distal end, an inflation lumen having a proximal portion adapted to establish fluid communication with the syringe assembly (3), and a distal end in fluid communication with the balloon (6), and a drainage lumen (not shown) adapted to drain fluid from the bladder during use, the syringe assembly (3) comprising a syringe part and a nozzle (11), the nozzle assembly comprising a pressure relief valve (9) adapted to exhaust fluid from the syringe assembly when the pressure reaches a threshold pressure, characterized in that the nozzle assembly additionally comprises a means, typically a stricture, for applying a resistance to flow of fluid, $R_f$, of 1.65E+11 to 1.85E+11 kg/m$^4$s. Preferably, the stricture comprises a narrow bore (12) of 0.04 mm$^2$ to 0.06 mm$^2$ cross sectional area disposed in the nozzle, ideally proximally of the pressure relief valve.

In a further aspect, the invention provides a syringe assembly, typically forming part of a catheter kit of the invention, the syringe assembly having a nozzle portion comprising a pressure relief valve (9) adapted to exhaust fluid from the syringe assembly when the pressure reaches a threshold pressure, characterized in that the nozzle portion additionally comprises a means, ideally a stricture, configured to provide a resistance to flow of fluid of 1.65E+11 to 1.85E+11 kg/m$^4$s. Preferably, the stricture comprises a narrow bore of 0.04 mm$^2$ to 0.06 mm$^2$ cross sectional area disposed in the nozzle proximally of the pressure relief valve.

In a further aspect, the invention provides a nozzle assembly forming part of the syringe assembly of the invention, the nozzle assembly comprising:
- a proximal end adapted to establish fluid communication with a nozzle of a syringe;
- a distal end adapted to establish fluid communication with a catheter;
- a lumen extending between the proximal and distal ends;
- a pressure relief valve in fluid communication with the lumen and adapted to exhaust fluid from the lumen when the fluid pressure in the lumen reaches a threshold pressure; and
- a stricture disposed in the lumen, preferably proximally of the pressure relief valve, configured to provide a resistance to flow of fluid of 1.65E+11 to 1.85E+11 kg/m$^4$s. Preferably, the stricture comprises a narrow bore of 0.04 mm$^2$ to 0.06 mm$^2$ cross sectional area.

The means for providing resistance to flow, typically a stricture, is suitably configured to provide a resistance to flow of 1.65E+11 to 1.85E+11 kg/m$^4$s, preferably 1.7E+11 to 1.8E+11 kg/m$^4$s, and ideally about 1.75E+11 kg/m$^4$s. This is calculated using Hagen Poisseuille Flow Theory. In a preferred embodiment, the stricture comprises a narrow bore, suitably a narrow bore of 0.04 to 0.06 mm$^2$, typically 0.045 to 0.055 mm$^2$, and ideally about 0.05 mm$^2$, cross sectional area. In one embodiment, the narrow bore comprises a cylindrical tube (although tubes or bores of other cross-sectional shapes are possible), having a length of 1-20 mm, typically 5-15 mm. In another embodiment, the narrow bore comprises an obstacle disposed in the lumen which has the effect of reducing the cross sectional area of the lumen at a point to 0.04 to 0.06 mm$^2$.

The syringe assembly may be formed in one, two or more parts. In one embodiment, the syringe part and nozzle assembly are formed as a single unitary structure. In another embodiment, first syringe part and a second nozzle assembly are separate parts adapted to engage together.

The term "balloon inflation pressure" means the pressure required to inflate the balloon when the balloon is located in the bladder. Typically, the balloon inflation pressure is less than 100 kPa, 110 kPa, 120 kPa, 130 kPa, 140 kPa, at an applied force of 3.5 kgF to 11.5 kgF. Typically, the balloon forming part of the catheter has an inflation pressure in the range of 50-100 kPa, 50-110 kPa, or 50-120 kPa, 50-130 kPa, 50-140 kPa, or 50-145 kPa, at an applied force of 3.5 kgF to 11.5 kgF.

Typically, the threshold pressure of the pressure release valve is about 5-15% greater than the balloon inflation pressure. Suitably, the threshold pressure is 100 to 150 kPa.

The pressure relief valve functions to vent fluid from the syringe assembly and release the pressure once it reaches a threshold pressure. The threshold pressure is greater than the balloon inflation pressure, generally about 5-20% greater. Pressure release valves are known in the art, as are syringes that incorporate pressure release valves. See for example WO95/33510.

The invention also provides a syringe assembly of the invention and a catheter, preferably a balloon catheter, ideally a transurethral balloon catheter.

The invention also provides a kit comprising a syringe, a nozzle of the invention, and a catheter. Preferably the catheter is a balloon catheter, ideally a transurethral balloon catheter.

The invention also relates to a transurethral catheter kit of the invention for use in the correct placement of a balloon catheter during a transurethral catheterization procedure, in which the balloon catheter is inserted into the urethra of a patient and threaded along the urethra until it is believed that the distal end of the catheter and balloon have entered the bladder, and depressing the plunger of the syringe to inflate the balloon, whereby the resistance means provides resistance to the depression of the plunger thereby inhibiting rapid depression of the plunger.

The invention as described in more detail below relates primarily to transurethral catheter kits, and syringe assemblies for use with transurethral catheters and use in transurethral catheterisation. However, it will be appreciated that the syringe assembly and nozzle of the invention are equally applicable for use with other types of balloon catheters, for example preventing over inflation of balloons during deployment of indwelling bowel catheters or intubation angioplasty procedures.

In one embodiment, the syringe assembly of the invention is for delivering a fluid to a patient, typically intravenously. The syringe assembly comprises a syringe part and a nozzle part, the nozzle part comprising a pressure relief valve (9) adapted to exhaust fluid from the syringe assembly when the pressure reaches a threshold pressure, characterized in that the nozzle portion additionally comprises means, ideally a stricture, configured to provide a resistance to flow of fluid of 1.65E+11 to 1.85E+11 kg/m$^4$s. Preferably, the stricture comprises a narrow bore of 0.04 mm$^2$ to 0.06 mm$^2$ cross sectional area disposed in the nozzle proximally of the pressure relief valve.

BRIEF DESCRIPTION OF THE FIGURES

The invention will be more clearly understood from the following embodiments thereof, given by way of example only, with reference to the accompanying drawings in which.

DETAILED DESCRIPTION OF THE INVENTION

Referring to the drawings, and initially to FIG. 1A, a transurethral catheter (TUC) assembly indicated generally by the reference numeral 1 comprises a catheter 2 and syringe assembly 3. The catheter 2 has a distal end 4, a proximal end 5, and an inflatable balloon 6 disposed on the distal end 4 having an inflation pressure (balloon inflation pressure) of 50-130 kPa depending on the force applied by the user to the syringe plunger. The catheter comprises an inflation lumen (not shown) in fluid communication at one end with the inflatable balloon 6 and at the other end with the syringe assembly 3. The catheter also includes a drainage lumen (not shown) adapted to drain urine from the bladder of a patient.

Referring to FIGS. 1B and 1C, a syringe assembly 3, according to the invention, comprises a syringe part having a barrel 7 and a plunger 8 adapted for tight but sliding movement within the barrel 7, and a nozzle part 11 having a pressure relief valve 9 adapted to exhaust inflation fluid from the barrel when the pressure in the syringe assembly reaches a threshold pressure of 120 kPa, and a stricture adapted to generate a resistance to flow in the fluid of $1.75E+11$ kg/m$^4$s. In this embodiment, the stricture is provided by a narrow bore 12 having a cross sectional area of 0.05 mm$^2$. The plunger 8 has an actuation rod 13 and a stopper 10. Although not shown in detail, the pressure release valve 9 comprises a valve head, a valve headset, and a helical spring that biases the valve head into engagement with the valve headset to close the valve and prevent venting of fluid from the syringe assembly. When the pressure in the fluid increases to a threshold pressure, the pressure in the fluid forces the valve head against the spring to open the valve and allow venting of fluid.

Figure 7:
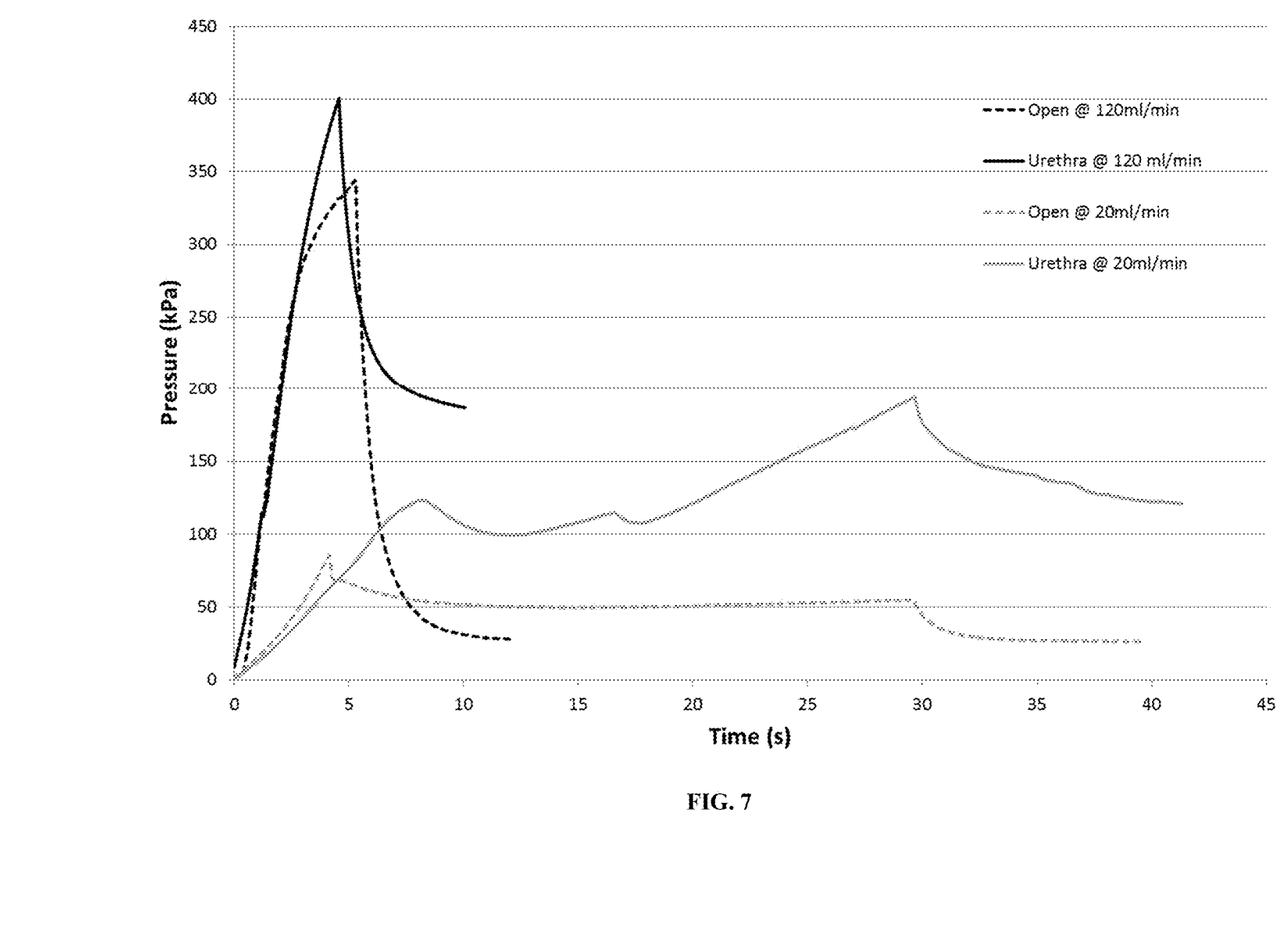
FIG. 7: Pressure vs. time for catheters inflated within the bladder (open) at 120 ml/min and 20 ml/min and in the urethra at 120 ml/min and 20 ml/min, to highlight the resistance caused by the urethra which will identify a pressure threshold range.

In use, the catheter is inserted into the urethra in a patients penis, and threaded along the urethra until the balloon at the distal end of the catheter is thought to be in the bladder. In order to anchor the catheter in situ, the balloon is then inflated by depressing the plunger in the syringe. Due to the presence of the narrow bore in the nozzle of the syringe, a resistance to flow of $1.75E+11$ kg/m$^4$s will be exerted on the fluid, which has the effect of maintaining the inflation pressure within a range of 65 kPa-135 kPa over an actuation force of 3.5 kgF to 11.5 kgF (FIG. 3), causing the balloon to inflate over a period of 12 to 27 seconds (FIG. 4). As indicated previously, this range of actuation forces spans the range of user variability, from use by a large powerful person to use by a small weak person. Thus, if an average user is inflating the balloon at a force of about 7.5 kgF, the inflation pressure would be likely to be in the 90-110 kPa range, with an inflation time of 17-22 seconds. If the balloon is located at the correct location, in the bladder, the balloon will continue to inflate until it is fully inflated with the inflation pressure never reaching the threshold pressure of the pressure relief valve of 120 kPa. However, if the balloon is incorrectly located, in the urethra, the resistance to inflation exerted by the walls of the urethra will necessitate that greater force is applied to the syringe plunger, causing the pressure in the fluid to increase above 120 kPa, and thereby actuating the valve to vent fluid from the syringe and release the pressure on the balloon. Thus, in this scenario, the pressure differential between normal inflation and actuation of the pressure release valve will be about 10-30 kPa, which is less than the pressure differential required to cause damage to the urethra (FIG. 7).

Experimental

User Variability

FIG. 2 displays the user variability exhibited within a group of 8 users using a normal syringe. This testing was performed on Coloplast 16Fr catheters and no attempt was made to control the flow rate which varies between approximately 19 and 70 ml/min. The flow rate of each user is a function of the force applied. To experimentally represent this variable force introduced by the users, 3 forces were selected from literature and identified as high, normal and low (11.5, 7.5 and 3.5 KgF respectively) which will be used in the next section of testing to highlight whether the flow rate control mechanism negates the effect of this variable force applied.

An experimental rig was then developed capable of applying these forces in a reliable and repeatable manner using ordinary syringes as well as the prototype. This rig was then used to determine the flow resistance that most appropriately controls flow rate to eliminate the user variability. FIGS. 3 and 4 display the effects of varying the flow resistance (by limiting flow rate) on the inflation pressure and time (respectively) using the predetermined weights (11.5 kgF-high, 7.5 kgF-normal and 3.5 kgF-low). It can be observed that increasing the flow resistance to $1.75E+11$ kg/m$^4$s results in the lowest variance between the three forces (FIG. 3) and also permits the inflation to be completed within a timeframe of approximately 12 to 27s depending on the force applied by the user (FIG. 4). This flow resistance, and the flow rate it generates, reduces the effect of user variability by limiting the inflation pressure to a range of between approximately 65 and 135 kPa (FIG. 3).

Manufacturing Variability

Figure 5:
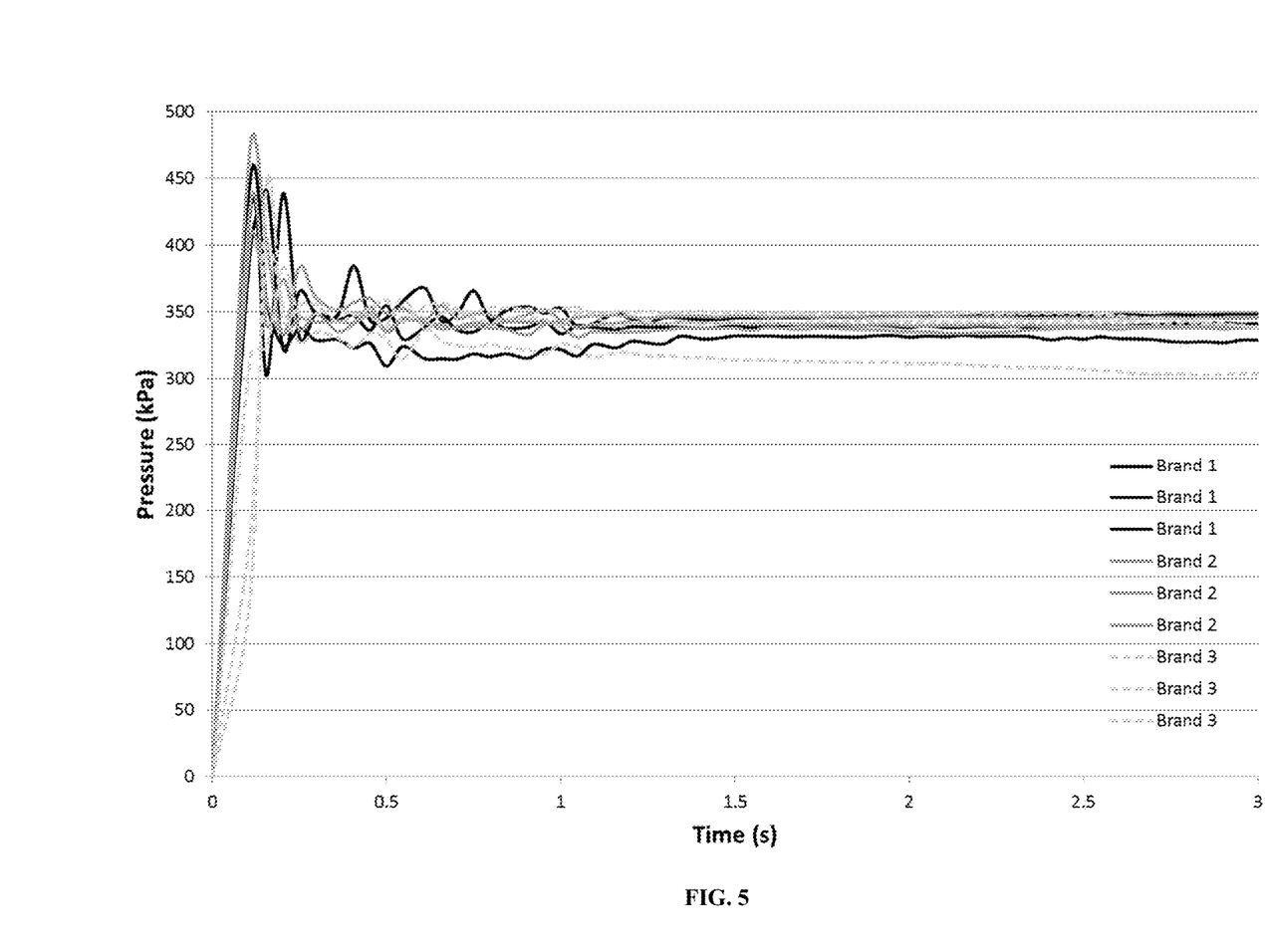
FIG. 5: Pressure vs. time of three brands (n=3, Coloplast, Bard and Medline) which highlights the reduction of variance in the pressure at the peaks between each catheter and each brand by using a constant applied force approach.

To address the issue of manufacturing variability, 5 brands of urinary catheter were selected and between 3 and 8 sizes of each were tested using the aforementioned rig. Three catheters were tested at each of the 3 previously mentioned forces. FIG. 5 displays the inflation profiles of 3 units of 3 brands at the normal force. As can be observed, the variance present between the 3 brands is inherently small after approximately 1 second which demonstrates that the use of the constant force concept produces results that minimise the effects of manufacture variability. However, the initial stages of inflation result in pressure spikes that vary between brands and result in an inflation peak pressure range of approximately 300-480 kPa.

Figure 6:
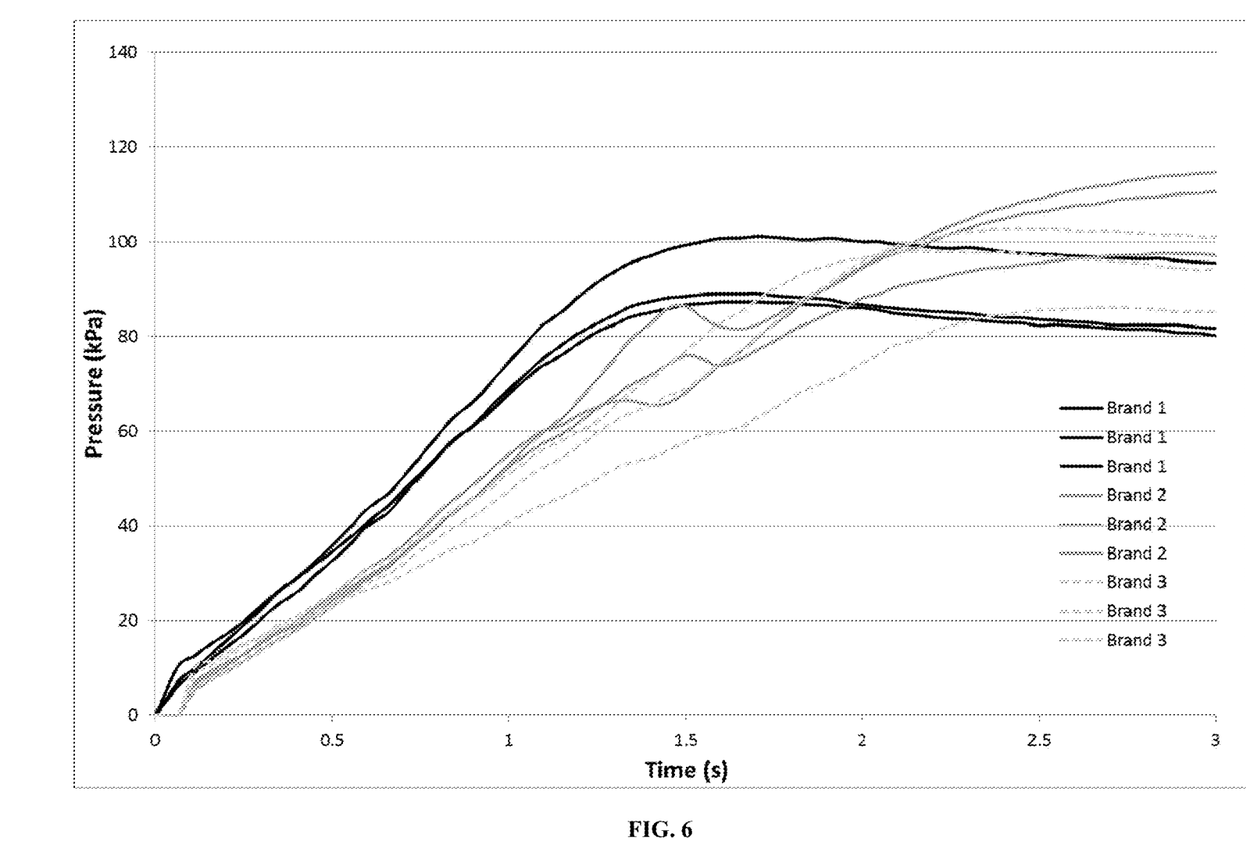
FIG. 6: Pressure vs. time of three brands (n=3, Coloplast, Bard and Medline) which highlights the reduction of peak pressure from approximately 500 kPa (FIG. 5) to approximately 120 kPa. Also, evident is the gradual increase in initial balloon pressure from the slope of the lines compared to the initial slopes seen in FIG. 5. These are made possible by employing the concept of applied resistance.

To examine the effect of the proposed resistance control, the tests were repeated with the flow rate controlling flow resistance in place. The results shown in FIG. 6 are for the normal force weight. As can be seen, the addition of the flow rate limiting flow resistance removes the sharp peaks and limits the peakpressures to a range of approximately 85-115 kPa. In addition to this the inclusion of flow resistance also reduces the maximum inflation pressure from nearly 500 kPa (FIG. 5) to just under 120 kPa (FIG. 6) and also increases the inflation time and generates a more steady inflation profile (evident from the initial slope of the graphs which is more vertical in FIG. 5 and more at an angle in FIG. 6 increasing the time to peak pressure from approximately 0.2 seconds to over 1.5 seconds). This increase in time for peak pressure allows time for the safety mechanism to activate if needed. The flow rate, limited by the flow resistance, therefore reduces the manufacturing variability significantly and, importantly, significantly reduces the pressures required to inflate the balloons.

Pressure Range and Threshold

To identify the pressure range within which the pressure valve must trigger, porcine urethras were obtained and tested. Catheters were inflated within the bladder and urethra sections of the porcine samples to identify the difference in pressure values, if any, in the bladder and urethra. The effect of varying the flow rate was also examined using a syringe pump to vary the inflation speed. FIG. 7 shows the results from this procedure.

This figure displays the pressure differential that exists between bladder and urethral inflation at two different flow rates. With the flow limited to 20 ml/min, a peak inflation pressure window of between 80 (bladder/open) and 125 kPa (urethra) exists during the first 10 seconds of inflation with the peak constrained (in the urethra) pressure increasing later in the inflation process to 190 kPa. This window shifts to 340 (bladder/open) and 400 kPa (urethra) for the higher flow rate. The results of this portion of the testing also revealed the influence of the urethra on the inflation pressures and at the highest flow rates an increase in pressure of 70 kPa is required to inflate the balloon within the urethra.

Testing has therefore revealed that using a flow resistance approach to controlling flow rate allows for user and manufacturing variability to be greatly reduced and brought within a controllable range. Testing has also revealed the range in which the pressure valve must operate and the effect of varying flow rate on this range. This pressure differential is applied to FIG. 3 to determine our operating window. It can be seen that the results in FIG. 7 for the highest flow rate of 120 ml/min results in the urethra applying a resistance to inflation which requires an increase in pressure of 70 kPa to inflate the balloon. At the lower flow rate the resistance applied by the porcine urethra reduces to 40 kPa. This is a significant finding as the porcine urethra applies a relatively low resistance to balloon inflation (corresponding to a maximum increase in inflation pressure of 70 kPa) when compared to the pressures typically applied using normal syringes and normal methods (approximately 400 kPa, FIG. 5). However, when flow resistance is included, the pressure required to inflate the balloon is significantly reduced and more importantly reduced to a level where the resistance applied by the urethra becomes comparable (85 kPa and 40 kPa from FIG. 7). Consequently, sensing the resistance provided by the urethra, should the user attempt to inflate the balloon in the urethra, is possible as the resistance pressure is approximately 50% of the inflation pressure. Further, applying these results to FIG. 3 demonstrates that the highest resistance used (1.75E+11 kg/m$^4$s) reduces the user variability (65-135 kPa) to a level where the resistance levels offered by the urethra can be used to actuate a safety valve. Therefore, our device, using resistance approaches, reduces user variability and manufacture variability in urethral catheterisation procedures to a level where sensing the urethral resistance to balloon inflation is possible and therefore the incorporation of a safety valve configured to sense these values will result in a safety device for transurethral catheterisation.

Cadeveric Testing

Figure 8:
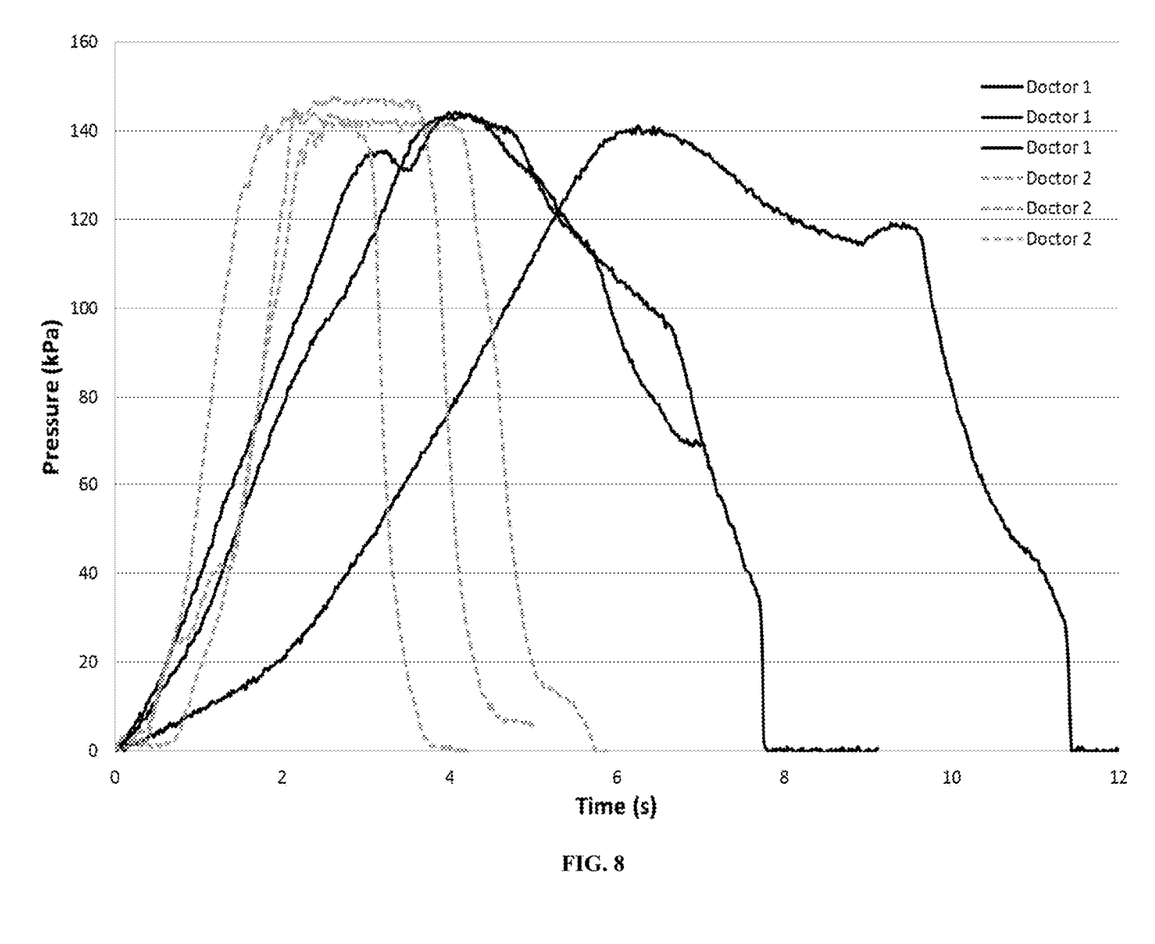
FIG. 8—Pressure vs time plots for one cadaver showing the results for each of the 2 urology specialist doctors and each of their 3 deployments highlighting the prototype valve actuation between 140-150 kPa in all cases.
Figure 9:
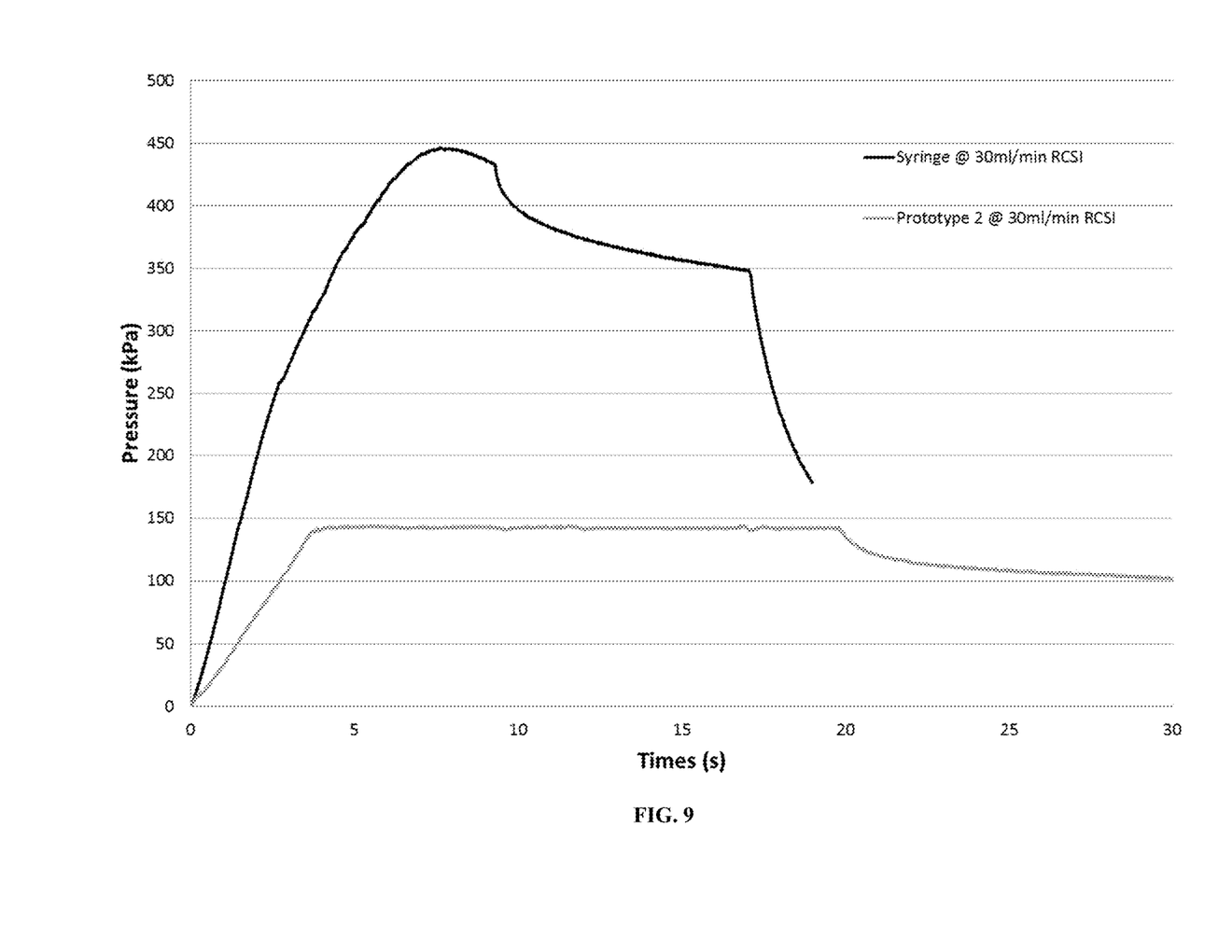
FIG. 9—Pressure vs time plot at a constant flow rate of 30 ml/min for both a normal syringe and the proposed safety device.

The results from the previous tests were employed to develop a prototype safety device that provided flow resistance at the determined level, see FIG. 1. A cadaver study was then carried out to assess the functionality and the efficacy of the device. Eight cadavers were used in the study and two urology specialist doctors carried out the testing. Each doctor deployed the device 3 times in each cadaver and an example of the results achieved for one cadaver are shown in FIG. 8. The balloon was intentionally placed in the urethra of the cadaver and inflated. It can be seen from the graph that the safety valve operated at approximately 140 kPa using this prototype in all cases. The balloon inflated until it touched the inside wall of the urethra at which time the urethra offers resistance to the balloon inflation increasing the pressure required to inflate the balloon. The pressure increased until the "popping" pressure of the valve was surpassed after which the inflation fluid vented out through the valve stopping the balloon inflation and damage to the urethra. A control test was also carried out using a syringe pump to control the flow rate to 30 ml/min and both a normal syringe and the prototype device were tested in this regime. These results can be seen in FIG. 9 where the pressure generated with the normal syringe reached approximately 450 kPa whereas it was again limited to under 150 kPa using the prototype device. In all instances of prototype device testing the valve actuated appropriately.

The invention is not limited to the embodiments hereinbefore described which may be varied in construction and detail without departing from the spirit of the invention.

The invention claimed is:

1. A transurethral catheter kit comprising a catheter (2) and a syringe assembly (3), the catheter having a distal end (4) and a proximal end (5), an inflatable balloon having a balloon inflation pressure (6) disposed on the distal end, an inflation lumen having a proximal portion adapted to establish fluid communication with the syringe assembly (3) and a distal end in fluid communication with the balloon, and a drainage lumen adapted to drain fluid from the bladder during use, the syringe assembly having a syringe and a nozzle (11), the nozzle comprising a pressure relief valve (9) adapted to exhaust fluid from the syringe assembly during delivery of the fluid from the syringe into the balloon when the pressure in the fluid reaches a threshold pressure, characterized in that the nozzle additionally comprises a narrow bore (12) disposed in the nozzle proximally of the pressure relief valve, the narrow bore having a resistance to flow $R_f$ of 1.65E+11 to 1.85E+11 kg/m$^4$s, thereby providing an inflation time for the balloon in the bladder of 12-27 seconds at an applied force of 3.5 kgF to 11.5 kgF, whereby the balloon inflation pressure is maintained within a range of 65 kPa to 135 kPa, and the threshold pressure of the pressure release valve is greater than a maximum balloon inflation pressure.

2. A transurethral catheter kit as claimed in claim 1 in which the nozzle is integrally formed with the syringe part.

3. A transurethral catheter kit as claimed in claim 2 in which the balloon inflation pressure is less than 130 kPa across an applied force of 3.5 kgF to 11.5 kgF, and the threshold pressure of the pressure release valve is at least 150 kPa.

4. A transurethral catheter kit as claimed in claim 2 in which the balloon inflation pressure is less than 100 kPa across an applied force of 3.5 kgF to 11.5 kgF, and the threshold pressure of the pressure release valve is at least 100 kPa.

5. A transurethral catheter kit as claimed in claim 1 in which the nozzle is separate from the syringe and is adapted to engage with the syringe to form the syringe assembly.

6. A transurethral catheter kit as claimed in claim 5 in which the balloon inflation pressure is less than 130 kPa across an applied force of 3.5 kgF to 11.5 kgF, and the threshold pressure of the pressure release valve is at least 150 kPa.

7. A transurethral catheter kit as claimed in claim 5 in which the balloon inflation pressure is less than 100 kPa across an applied force of 3.5 kgF to 11.5 kgF, and the threshold pressure of the pressure release valve is at least 100 kPa.

8. A transurethral catheter kit as claimed in claim 1 in which the balloon inflation pressure is less than 130 kPa across an applied force of 3.5 kgF to 11.5 kgF, and the threshold pressure of the pressure release valve is at least 150 kPa.

9. A transurethral catheter kit as claimed in claim 1 in which the balloon inflation pressure is less than 100 kPa across an applied force of 3.5 kgF to 11.5 kgF, and the threshold pressure of the pressure release valve is at least 100 kPa.

10. A syringe assembly comprising a syringe and a nozzle, the syringe assembly being configured for attachment to a catheter having an inflatable balloon, the balloon having an inflation pressure, the nozzle comprising a pressure relief valve (9) adapted to exhaust fluid from the syringe assembly while delivering the fluid from the syringe when the pressure in the fluid reaches a threshold pressure, characterized in that the nozzle additionally comprises a narrow bore of 0.04 mm$^2$ to 0.06 mm$^2$ cross sectional area disposed in the nozzle proximally of the pressure relief valve, the narrow bore having a resistance to flow $R_f$ of 1.65E+11 to 1.85E+11 kg/m$^4$s, whereby, in use, the syringe assembly delivers the fluid to an attached catheter and inflates the balloon over a time of 12-27 seconds at an applied force of 3.5 kgF to 11.5 kgF, whereby the pressure of the delivered fluid is maintained within a range of 65 kPa to 135 kPa, and the threshold pressure of the pressure release valve is greater than a maximum balloon inflation pressure.

11. A syringe assembly as claimed in claim 10 in which the nozzle is integrally formed with the syringe.

12. A syringe assembly as claimed in claim 10 in which the nozzle is configured for retro-fitting to the syringe to form the syringe assembly.

13. A syringe assembly as claimed in claim 10 in which the threshold pressure of the pressure release valve is 100 to 150 kPa.

14. The syringe assembly of claim 10, wherein the nozzle is separate from the syringe and is adapted to engage with the syringe to form the syringe assembly.

15. The syringe assembly of claim 10, wherein the threshold pressure of the pressure relief valve is at least 100 kPa.

16. The syringe assembly of claim 15, wherein the threshold pressure is at least 150 kPa.

17. A nozzle for a syringe assembly, the nozzle comprising:
 a proximal end adapted to establish fluid communication with a syringe;
 a distal end adapted to establish fluid communication with a catheter;
 a lumen extending between the proximal and distal ends;
 a pressure relief valve in fluid communication with the lumen and adapted to exhaust fluid from the lumen while delivering a fluid from the syringe when a fluid pressure in the lumen reaches a threshold pressure; and
 a narrow bore of 0.04 mm$^2$ to 0.06 mm$^2$ cross sectional area disposed in the lumen proximally of the pressure relief valve, the narrow bore having a resistance to flow $R_f$ of 1.65E+11 to 1.85E+11 kg/m$^4$s, thereby delivering the fluid from the syringe over a time of 12-27 seconds at an applied force of 3.5 kgF to 11.5 kgF, whereby the pressure of the delivered fluid is maintained within a range of 65 kPa to 135 kPa, and the threshold pressure of the pressure release valve is greater than a maximum fluid delivery pressure.

* * * * *